United States Patent [19]

Ascher

[11] Patent Number: 4,809,705
[45] Date of Patent: Mar. 7, 1989

[54] PORTABLE ELECTROCARDIOGRAM MONITOR

[76] Inventor: Gilles Ascher, 20bis bd du General Leclerc, 92200 Neuilly sur Seine, France

[21] Appl. No.: 785,576

[22] Filed: Oct. 8, 1985

[30] Foreign Application Priority Data

Oct. 11, 1984 [FR] France ............................ 84 15594

[51] Int. Cl.[4] .............................................. A61B 5/04
[52] U.S. Cl. ..................................... 128/710; 128/639
[58] Field of Search .............. 128/695, 696, 697, 701, 128/702–703, 704, 706, 710, 712, 419 PT, 903, 639, 644

[56] References Cited

U.S. PATENT DOCUMENTS

| | | | |
|---|---|---|---|
| 2,685,881 | 8/1954 | Kelly | 128/644 |
| 3,613,670 | 10/1971 | Edenhofer | 128/701 |
| 3,776,228 | 12/1973 | Semler | 128/710 |
| 3,848,582 | 11/1974 | Milani et al. | 128/712 |
| 4,476,869 | 10/1984 | Bihn | 128/419 PT |
| 4,535,783 | 8/1985 | Marangoni | 128/639 |
| 4,606,352 | 8/1986 | Geddes et al. | 128/712 |

*Primary Examiner*—William E. Kamm
*Attorney, Agent, or Firm*—Bachman & LaPointe

[57] ABSTRACT

A portable electrocardiogram recorder is formed from a case containing a device for the digital processing of signals taken by means of at least two electrodes in contact with the skin of the patient.

One of the faces of application of said case comprises projecting electrodes in the form of protuberances on said face, said electrodes comprising cavities whose shape is complementary to that of the stud of the usual electrocardiogram electrodes fixed by adhesion to the skin of the patient, thus ensuring both mechanical and electrical coupling, so that said case may be applied either directly to the skin of the patient or indirectly through usual electrodes.

1 Claim, 1 Drawing Sheet

PORTABLE ELECTROCARDIOGRAM MONITOR

BACKGROUND OF THE INVENTION

1. Field of the Invention

The present invention relates to a portable electrocardiogram recorder, namely an apparatus formed essentially from a case containing a device for the digital processing of signals picked up by at least two electrodes in contact with the skin of the patient, read and analyzed subsequently by a doctor.

2. Description of the Prior Art

Apparatus of this type are already known which comprise pick up electrodes formed by small conducting plates disposed in one of the faces of the apparatus. These apparatus are intended to record a few electrocardiograms on appearance of a malaise or indisposition, the patient then placing the electrodes in contact with his skin, for example by gripping the apparatus between his two hands when he feels a malaise. It is also possible to make a precordial recording by placing the electrodes on the thorax. However, in this case the quality of the contact may be uncertain because of the profile of the bust of the patient and because of the inevitable variations in pressure exerted, by the patient or a third party (during application of the apparatus). In addition, such a situation is only conceivable for very short recordings to the extent that it implies pressing the apparatus on the thorax.

Furthermore, it is desirable for the apparatus to be able to be used "in real time" i.e. for example in the consulting room of a doctor; in this case it is necessary to be able to display the signals obtained directly on the apparatus so as to avoid having to pass through an external apparatus which reads the memory and restores the electrocardiogram signals.

OBJECT OF THE INVENTION

An object of the present invention is to provide a recorder of the above mentioned type which allows a good contact of the electrodes to be obtained when taking electrocardiograms in the pericardial zone, which allows the recorder to be held in the operating position and which allows it to be used in real time.

SUMMARY OF THE INVENTION

The recorder of the invention is more especially remarkable in that at least one of the faces of application of the case comprises projecting electrodes forming protuberances on said face, these electrodes comprising cavities whose shape is complementary to that of the studs of the usual electrocardiogram electrodes fixed by adhesion to the skin of the patient, thus ensuring both mechanical and electrical coupling, so that said case may be applied either directly to the skin of a patient or indirectly through usual electrodes. The invention provides then an apparatus which may be used rapidly by placing it on the chest of a patient and which may also be fixed permanently to a patient using usual electrodes of the disposable type, consequently in a simple an inexpensive way.

According to another feature of the invention, the recorder comprises a display device disposed on the face opposite the face of application of the electrodes and a microprocessor controlling said display device. With such a display device, the recorder can be operated in "real time", that is to say that the form of the electrocardiogram signals recorded may be followed during recording thereof. Such a device in particular allows a first diagnosis to be made during a visit to a patient.

Advantageously, the display device comprises an image holding device, which allows a more accurate analysis of the recorded signals The recorder of the invention advantageously comprises a memory in which the recorded electrocardiogram signals are stored in digital form, which provides a more complete supervision of a patient

BRIEF DESCRIPTION OF THE DRAWINGS

Other features and advantages of the invention will be clear from the following description given by way of illustration with reference to the accompanying drawings in which.

DESCRIPTION OF THE PREFERRED EMBODIMENT

Figure 3:
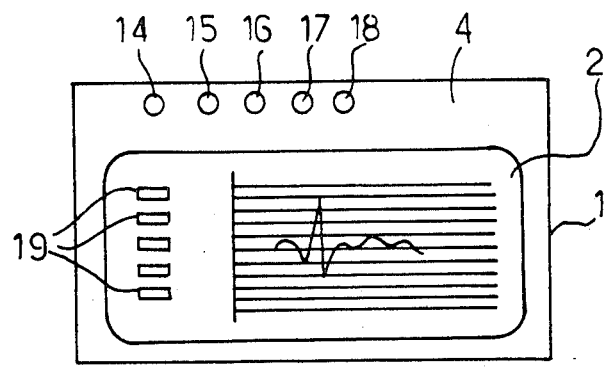
FIG. 3 is a top view of the recorder of FIG. 1.
Figure 2:
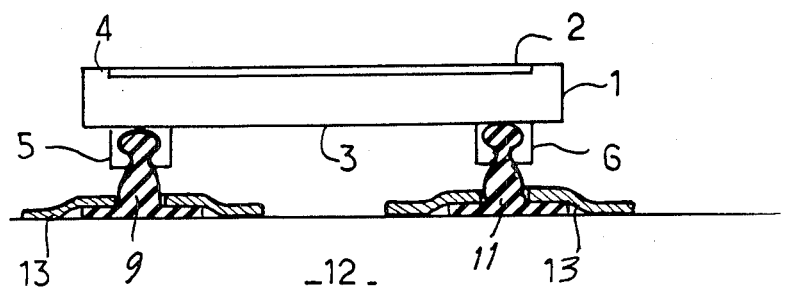
FIG. 2 shows the recorder of FIG. 1 fixed to a patient by means of usual electrodes of the disposable type.
Figure 1:
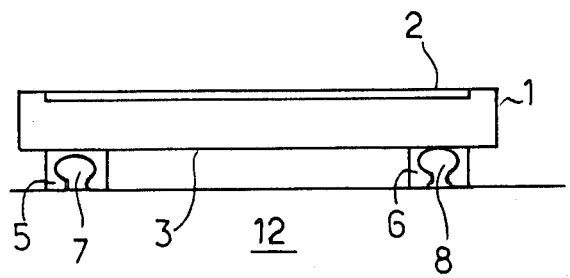
FIG. 1 is a side view of a recorder in accordance with the present invention in position on a patient.

In FIGS. 1 to 3 can be seen a recorder which is formed from a small sized case 1, one of whose faces comprises a display device 2 formed for example by a liquid crystal screen; on the face of application 3 which is opposite face 4 carrying screen 2 are disposed at least two electrodes 5 or 6, for example three electrodes one of which forms the reference electrode. Electrodes 5 and 6 project from face 3 and form protuberances on this face. They comprise cavities 7 and 8 opening out on the side opposite the face of application and whose shape corresponds to the shape of the studs for fixing the usual electrocardiogram electrodes of the disposable type. With such an arrangement, usual disposable electrodes 9 and 11 may be fixed to the electrodes 5 and 6 of the case which may then be permanently fixed to the skin 12 of the patient as shown in FIG. 2. Because of the low weight of case 1, two or three usual electrodes are sufficient for holding the case on the body of the patient even if this latter moves. In fact, the usual disposable electrocardiogram electrodes 9 and 11 comprise an adhesive disk 13 which is stuck to the skin 12 of the patient.

The recorder of the invention comprises a microprocessor which is housed in case 1 and which controls the operation of the display device as well as the processing of the electrocardiogram signals taken.

Advantageously, the recorder also comprises a memory in which are stored in digital form the electrocardiogram signals taken by means of electrodes 5 and 6.

Control 14 allows recording of the electrocardiograms taken to be obtained, storage taking place permanently as long as this control 14 is actuated, the storage being made in accordance with the "first in first out" mode.

A switch 15 with two stable positions controls the on off switching of the recorder of the invention. During operation, the display device 2 displays the shapes of the signals collected; the travelling speed thereof may be adjusted by means of a control member 16 and a control member 17 allows an image to be held, i.e. the display of a fixed image.

When the recorder comprises a memory it is possible to display the contents of the memory and, so as to avoid complicated operations, the recorder comprises a control means 18 which controls the reading before or after the memory.

Advantageously, the electronic processing device comprises a device for calculating the heart beat rate which calculates said rate for example by detecting three QRS fronts of three successive electrocardiograms. In this case, the display device 2 further displays the heart beat rate of the subject and it may comprise an element winking at the frequency of the heart beat rate of the electrocardiogram taken.

The recorder of the invention may comprise output connections to a printer or to a conventional electrocardiogram apparatus or else both possibilities.

In another variant of the recorder of the invention, the electronic processing device effects an analysis of the electrocardiogram signals taken and calculates their different parameters which are then displayed simultaneously on the display screen 2; in FIG. 3 can be seen the screen 2 which displays on the one hand an electrocardiogram and on the other, at positions 19, the different parameters of the electrocardiogram as well as the frequency of the heart beat rate.

Furthermore, the recorder of the invention may comprise a device for monitoring the heart beat rate comprising a sound and/or visual alarm which is tripped when the heart beat rate exceeds adjustable upper and lower limit values.

The recorder which has just been described may be used in different ways. In a first version, comprising essentially the display device with the different controls and with the display of the heart beat rate, the recorder may be used by general practitioners during their visit or by doctors in emergency services; in this case the apparatus is used without disposable electrodes, the doctor applies it to the chest of the patient and he may immediately observe the form of the electrocardiograms and know the heart beat rate, which allows him to rapidly detect the possibility of a cardiac deficiency and to send the patient immediately to a service having equipment available for cardiological diagnosis.

In another use, in a version comprising a memory, the recorder of the invention may be used in the consulting room of the practitioner, for example for monitoring the operation of a pace maker; in this case, the memory allows the form of the electrocardiogram to be carefully examined for the whole time required either directly on the apparatus or on an external electrocardiogram analysis apparatus using the connection provided for this purpose. In the case where a connection to a printer is made, the program of the electronic processing device of the recorder is adapted so that the printer prints an electrocardiogram in the form of a conventional electrocardiogram, i.e. with coordinate axes and squares giving immediately the value of the recorded signals. In this use, the recorder may be applied directly or through disposable type conventional electrodes. Furthermore, it is always possible, for monitoring a pacemaker, to display the form of the pulses delivered by the pacemaking and to effect an oscilloscope analysis comprising display of the pulse and display of the principle parameters:

pulse width
stimulation frequency and interval
auriculo-ventricular delay.

The recorder of the invention may also be used as an apparatus for monitoring a patient, for example during small operations (by connecting the apparatus to electrodes placed on the patient by means of a connecting cable) in which the practitioner desires to operate without any risk or also for transporting patients to a hospital or inside a hospital (in this use, the recorder is permanently placed on the patient and disposable type electrodes are then used for fixing the recorder on the patient). The recorder of the invention forms a portable monitoring apparatus which permanently displays the form of the electrocardiograms of the patient and which gives an alarm when the heart beat rate reaches a predetermined threshold.

What is claimed is:

1. A portable electrocardiogram monitor comprising a housing having a first face with a plurality of signal input means projecting therefrom for receiving electrocardiographic signals, microprocessing means contained within said housing for processing said electrocardiographic signals appearing on said signal input means, said housing having a second face having a display device for displaying the processed signal, the improvement which comprises said signal input means having surfaces for contact with a patient's chest, said surfaces having undercut cavities for receiving studs provided on disposable electrodes on said plurality of signal input means.

* * * * *